US007662571B2

(12) United States Patent
Elgebaly et al.

(10) Patent No.: US 7,662,571 B2
(45) Date of Patent: Feb. 16, 2010

(54) MITOCHONDRIAL MARKERS OF ISCHEMIA

(75) Inventors: Salwa A. Elgebaly, Edgewater, MD (US); Elliott Schiffmann, Chevy Chase, MD (US)

(73) Assignee: Nourheart Inc., Edgewood, MD (US)

( * ) Notice: Subject to any disclaimer, the term of this patent is extended or adjusted under 35 U.S.C. 154(b) by 0 days.

(21) Appl. No.: 11/486,741

(22) Filed: Jul. 13, 2006

(65) Prior Publication Data

US 2007/0015212 A1    Jan. 18, 2007

Related U.S. Application Data

(60) Provisional application No. 60/698,934, filed on Jul. 14, 2005.

(51) Int. Cl.
*G01N 33/53* (2006.01)
(52) U.S. Cl. .......................... 435/7.1; 435/7.2; 436/517
(58) Field of Classification Search ................. 435/7.1, 435/7.2, 7.92; 436/518
See application file for complete search history.

(56) References Cited

U.S. PATENT DOCUMENTS

| | | | |
|---|---|---|---|
| 5,091,404 A | 2/1992 | Elgebaly | |
| 5,270,163 A | 12/1993 | Gold et al. | |
| 5,403,914 A | 4/1995 | Elgebaly | |
| 5,504,013 A | 4/1996 | Senior | |
| 5,606,027 A * | 2/1997 | Elgebaly | 530/389.2 |
| 5,622,871 A | 4/1997 | May et al. | |
| 6,235,241 B1 | 5/2001 | Catt et al. | |
| 6,399,398 B1 | 6/2002 | Cunningham et al. | |
| 6,670,138 B2 * | 12/2003 | Gonzalez-Zulueta et al. | 435/7.1 |
| 2005/0137481 A1 * | 6/2005 | Sheard et al. | 600/508 |

FOREIGN PATENT DOCUMENTS

| | | |
|---|---|---|
| WO | WO 91/19813 | 12/1991 |
| WO | WO 92/05285 | 4/1992 |
| WO | WO 92/14843 | 9/1992 |
| WO | WO 03/074069 | 9/2003 |

OTHER PUBLICATIONS

Lutsenko et al. Proc. Natl. Acad. Sci. 1998 vol. 95, p. 6004-6009.*
Koehler et al. Proc. Natl. Acad. Sci. 1999 vol. 96. page 2141-2146.*
Burgess et al (J Cell Biol. 111:2129-2138, 1990).*
Beattie M.S., Trends in Molecular Medicine, 2004, vol. 19, No. 12, pp. 580-583.
Yamazaki et al., European Journal of Pharmacology, 2001, vol. 413, pp. 173-178.
O'Flaherthy et al., The Journal of Immunology, 1978, vol. 120, No. 4, pp. 1326-1332.
Le et al., Trends in Immunology, 2002, vol. 23, No. 11, pp. 541-548.
Alpert, J.S. et al., "Myocardial Infarction Redefined—A Consensus Document of The Joint European Society of Cardiology/American College of Cardiology Committee for the Redefinition of Myocardial Infarction," J. Am. Coll. Cardiol. 2000; 36; 959-69.
Boersma, E. et al., "Platelet glycoprotein IIb/IIa inhibitors in acute coronary syndromes: a meta-analysis of all major randomized clinical trials," Lancet 2002:359: 189-98.
Brennan, M.L. et al., "Prognostic Value of Myeloperoxidases in Patients with Chest Pain," N. Engl. J. Med. 2003: 349:1595-604.
Christenson, R.H. et al., "Characteristics of an Albumin Cobalt Binding Test for Assessment of Acute Coronary Syndrome Patients: A Multicenter Study," Clin. Chem. 2001; 47:464-470.
Christenson, R.H. And Azzazy, H.M.E., "Biochemical markers of acute coronary syndromes," Clin. Chem., 44, 1855-64, 1998.
Danne, O. et al., "Prognostic Implications of Elevated Whole Blood Choline Levels in Acute Coronary Syndrome," Am. J. Cardiol. 2003; 91: 1060-7.
de Lemos, J.A. et al., "The Prognostic Value of Serum Myoglobin in Patients with Non-ST-Segment Elevation Acute Coronary Syndromes," J. Am. Coll. Cardiol. 2002; 40: 238-44.
Doherty, D.E. et al., "Human Monocyte Adherence: A Primary Effect of Chemotactic Factors on the Monocyte to Stimulate Adherence to Human Endothelium," J. Immunol. 138(6), 1762-1771, 1987.
Elgebaly, S.A. et al., "Cardiac Derived Neutrophil Chemotactic Factors; Preliminary Biochemical Characterization," J. Mol. Cell Cardiol., 21:585-593, 1989.
Elgebaly, S.A. et al., "Cyclocreatine Inhibits the Production of Nutrophil Chemotactic Factors from Isolated hearts," Am. J. Pathol. 137: 1233-1241, 1990.
Elgebaly, S.A. et al., "Cardiac-derived neutophil chemotactic factors: Detection in coronary sinus effluents of patients undergoing myocardial revascularization," J. Thorac. Cardiovasc. Surg., 130(5): 952-959, 1992.
Elgebaly, S.A. et al., "Evidence of Cardiac Inflammation After Open Heart Operations," Ann. Thorac. Surg., 57:391-396, 1994.
Joyce, "Amplification, mutation and selection of catalytic RNA" (1980) Gene 82:83-87.
Kleinfeld, A.M. et al., "Increases in Serum Unbound Free Fatty Acid Levels Following Coronary Angioplasty," Am. J. Cardiol., 1996, 78:1350-4.
Lucchesi, B.R. et al., "Leukocytes and Ischemia-induced Myocardial Injury," Annu. Rev. Pharmacol. Toxicol., 26: 201-224, 1986.
Newby, L.K. et al., "Bedside Multimarker Testing fr Risk Stratification in Chest Pain Units," Circulation, 2001, 103:1832-7.
Szostak et al., "In vitro selection of RNA molecules that bind specific ligands," (1990) Nature 346:818-822.

(Continued)

*Primary Examiner*—Jacob Cheu
(74) *Attorney, Agent, or Firm*—Latimer & Mayberry IP Law, LLP

(57) ABSTRACT

Damage to tissue, such as ischemic damage, can cause the release of mitochondrial proteins. The released proteins can be detected in a sample taken from a subject, indicating that the subject has suffered damage.

10 Claims, 3 Drawing Sheets

OTHER PUBLICATIONS

Tuerk et al., "Systematic Evolution of Ligands by Exponential Enrichment: RNA Ligands to Bacteriophage T4 DNA Polylmerase" (1990) Science 249:505-510.

Yamamoto, Yuri et al., "Inhibitory Effects of Spinorphin, a Novel Endogenous Regulator, on Chemotaxis, O2 Generation, and Exocytosis by N-Formylmethionyl-leucyl-phenylalanine (FMLP)-Stimulated Neutrophils," Biochemical. Pharmacology, 54; 695-701, 1997.

Trueba et al. (J. Bacteriology 1992 vol. 174, p. 4761-4768.

* cited by examiner

MITOCHONDRIAL MARKERS OF ISCHEMIA

CROSS REFERENCE TO RELATED APPLICATIONS

This application claims priority to U.S. Application No. 60/698,934, filed Jul. 14, 2005.

TECHNICAL FIELD

This application relates to markers of cardiac damage, particularly to mitochondrial markers of cardiac damage.

BACKGROUND

Cardiac markers serve an important role in the early detection and monitoring of cardiovascular disease. Markers of disease are typically substances found in a bodily sample that can be easily measured. The measured amount can correlate to underlying disease pathophysiology, presence or absence of a current or imminent cardiac event, probability of a cardiac event in the future. In patients receiving treatment for their condition, the measured amount will also correlate with responsiveness to therapy. Markers can include elevated levels of blood pressure, cholesterol, blood sugar, homocysteine and C-reactive protein (CRP). However, current markers, even in combination with other measurements or risk factors, do not adequately identify patients at risk, accurately detect events (i.e., heart attacks), or correlate with therapy. For example, half of patients do not have elevated serum cholesterol or other traditional risk factors.

Myocardial ischemia can be a main cause of the acute coronary syndromes (ACS), a continuum of disease that spans from unstable angina (characterized by reversible cardiac ischemia) to myocardial infarction with large areas of necrosis. Myocardial ischemia can result from thrombus formation after plaque rupture in a coronary artery. The acute coronary syndromes represent a complex and heterogeneous physiological condition. Although remarkable therapeutic and technological advances over the past 20 years have reduced the in-hospital mortality of acute myocardial infarction, this progress has been limited to patients who display ST-elevation on their electrocardiogram (ECG). ST-elevation is an indicator of myocardial infarction, and treatment within 12 hours of symptoms onset will improve the outcome. However, only about 50% of myocardial infarction patients have diagnostic ECG changes. The remaining patients must be observed for clinical monitoring signs and biochemical markers such as cardiac troponin T or 1.

Cardiac troponin has become the cornerstone for diagnosis of myocardial infarction. Markers such as CK-MB and myoglobin can be useful for assessment and risk stratification of suspected ACS patients. Compelling evidence indicates that an elevated cardiac troponin can identify high-risk ACS patients that benefit from treatment with antiplatelet agents including; inhibitors of the glycoprotein IIb/IIIa platelet receptor (such as abciximab, eptifibatide, lamifiban and tirofiban), COX II inhibitors (such as acetylsalycilic acid) and ADP receptor antagonists (such as clopidogrel and ticlopidine). However, troponin, CK-MB and myoglobin are markers of necrosis and therefore offer no information regarding myocardial ischemia that occurred before cell death. A test that can accurately detect the presence or absence of myocardial ischemia allowing treatment decisions to be made at an earlier stage of the ACS continuum will have significant clinical utility. Further, therapeutic options specifically targeting this early stage of ACS has the potential to significantly improve patient prognosis.

SUMMARY

Eukaryotic cells contain mitochondria, organelles that produce energy for the cell. In multicellular organisms, different types of cells can have different numbers of mitochondria. For example, in animals, muscle cells can have a high number of mitochondria, in order to provide energy for muscle function. Injury to cells, tissues or organs can cause disruption of mitochondria and the release of their contents.

Muscle cells (e.g., myocardial cells) contain a high proportion of muscle proteins (e.g., actin, myosin, troponin) and mitochondria devoted to producing energy to drive muscle contraction. Damage to myocardial cells, such as occurs when the myocardium is subject to ischemia, can cause the contents of the cells to be released. The cellular contents can be detected in other bodily samples (for example, in the blood). In particular, mitochondria can be disrupted, and the contents of the mitochondria can be detected elsewhere. These detectable components of mitochondria can be diagnostic of cardiac damage. A mitochondrial polypeptide (i.e., a peptide normally localized in mitochondria and including at least two amino acid residues) can be one such component diagnostic of cardiac damage.

In one aspect, a method of detecting ischemia includes obtaining a sample from a subject suspected to have a ischemia and assaying the sample for a mitochondrial polypeptide. The subject can be a human subject, or a non-human subject such as, for example, a bird, a mouse, a rat, a rabbit, a pig, a sheep, a goat, a cow, or another mammal. A mitochondrial polypeptide can be encoded by mtDNA, or encoded by nuclear DNA and transported to the mitochondria after translation. The mitochondrial polypeptide can be a formyl peptide receptor (FPR) ligand. An FPR ligand can optionally include an N-formyl group, for example, N-formyl methionine. The FPR ligand can be derived from a mitochondrial polypeptide. For example, the FPR ligand can be a breakdown product (e.g., a hydrolysis product) of a mitochondrial polypeptide. The FPR ligand can be Nourin-1. The mitochondrial polypeptide can be an N-formyl polypeptide, a peptide encoded by mtDNA, an FPR ligand, or Nourin-1. Detection of a predetermined amount of the mitochondrial polypeptide can be indicative of cardiac ischemia.

In another aspect, a method of detecting ischemia includes obtaining a sample from a subject suspected to have a cardiac injury and assaying the sample for an N-formyl polypeptide. The N-formyl polypeptide can be a mitochondrial polypeptide. The mitochondrial polypeptide can be a polypeptide encoded by mtDNA or nuclear DNA. The mitochondrial polypeptide can be an FPR ligand, or Nourin-1.

The details of one or more embodiments are set forth in the accompanying drawings and the description below. Other features, objects, and advantages will be apparent from the description and drawings, and from the claims.

DETAILED DESCRIPTION

Figure 1:
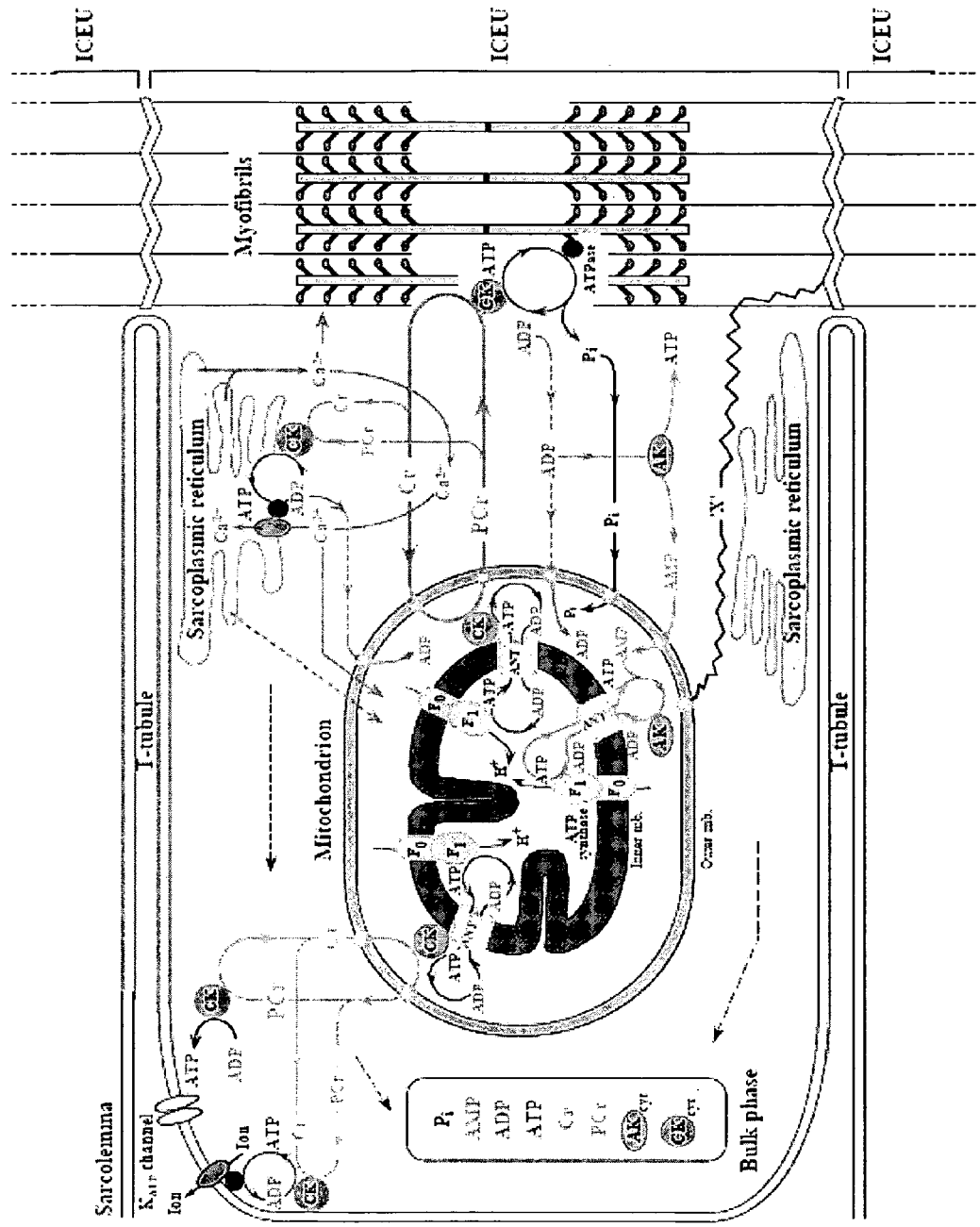
FIG. 1 is a schematic diagram depicting metabolic pathways in muscle tissue.

Nourin-1 is a neutrophil chemoattractant present in cardioplegic samples and clinical specimens from patients experiencing reversible and irreversible ischemia (see, for example, U.S. Pat. No. 5,403,914, which is incorporated by reference in its entirety). Nourin-1 is heat labile and degraded by proteolytic enzymes. Its chemoattractant activity is associated with a low molecular weight (mwt) protein fraction (described as 0.5-5 kDa in U.S. Pat. No. 5,403,914) and a high mwt protein fraction (described as 100-300 kDa in U.S. Pat. No. 5,403,914) characterized and separated by gel filtration. Antibodies have previously been developed against a protein sample purified by isoelectric focusing (IEF) (pI 7-8). These antibodies remove a chemotactic factor from the IEF-purified sample. The IEF-purified protein included a 3 kDa and a 6 kDa species. The 6 kDa species is believed to be a dimer of the 3 kDa species. Some chemoattractants (e.g. IL-8) do exist as both monomer and a dimer. Other chemoattractant Nourins are released from other tissues.

It is believed that the low mwt chemoattractant is a deletion or dissociation product of the high mwt chemoattractant. While this remains a hypothesis, rapid generation of opioid peptides from endogenous proteins has been characterized in milk protein, mitochondrial cytochrome b, and hemoglobin. See, for example, Teschemacher, H., G. Koch, and V. Brantl. 1997. *Milk protein-derived opioid receptor ligands. Biopolymers* 43:99; Zadina, J. E., A. J. Kastin, L. J. Ge, and V. Brantl. 1990. *Hemorphins, cytochrophins, and human-casomorphins bind to antiopiate (TYR-MIE-1) as well as opiate binding sites in rat brain. Life Sci.* 47:PL25; and Brantl, V., et al. 1985. *Novel opioid peptides derived from mitochondrial cytochrome b: cytochrophins. Eur. J. Pharmacol.* 111:293, each of which is incorporated by reference in its entirety.

Identification of the target receptor for the low mwt chemoattractant might be possible through the knowledge that chemotaxis of neutrophils caused by the low mwt chemoattractant is inhibited by spinorphin. Spinorphin is an endogenous heptapeptide with amino acid sequence identical to a conserved region of the beta-chain of human hemoglobin (see, for example, Liang T S, Gao J L, Fatemi O, Lavigne M, Leto T L, Murphy P M. *The endogenous opioid spinorphin blocks fMet-Leu-Phe-induced neutrophil chemotaxis by acting as a specific antagonist at the N-formylpeptide receptor subtype FPR. J Immunol.* 2001 Dec. 1; 167(11):6609-14, which is incorporated by reference in its entirety). The properties of the putative receptor for N-formyl chemotactic peptides in rabbit neutrophils have been studied (see, e.g., Schiffmann E; *Some characteristics of the neutrophil receptor for chemotactic peptides. FEBS Lett.* 1980 Aug. 11; 117(1):1-7, which is incorporated by reference in its entirety). The binding of peptides to the receptor correlated with the cell's chemotactic responsiveness and lysosomal enzyme-releasing capacity. Spinorphin targets the N-formyl-peptide receptor (FPR) on neutrophils suggesting that this might be the receptor involved in low mwt chemoattractant binding. Spinorphin is rapidly released by cleavage from a larger protein (P-hemoglobin), again demonstrating a parallel with the idea that the low mwt chemoattractant is a cleavage product from the high mwt protein. See, e.g., Liang et al., *J. Immunol.* 2001 Dec. 1; 167(11):6609-14.

Spinorphin is known as a modulator of FPR, and its existence indicates that there is an agonist for the receptor that has not yet been found. Although spinorphin is specific for FPR, it lacks an N-formyl methionine motif (spinorphin has the amino acid sequence Leu-Val-Val-Tyr-Pro-Trp-Thr; SEQ ID NO:1).

Inhibition by spinorphin can be used to distinguish ligands to FPR from ligands that bind to two related receptors, referred to as FPR-like 1 (FPRL1) and FPR-like 2 (FPRL2). These receptors, unlike FPR, are low-affinity receptors for the agonist formyl-Met-Leu-Phe (fMLP) and are only activated by high (micromolar) concentrations. See, for example, Gao, J. L., and P. M. Murphy. 1993. *Species and subtype variants of the N-formyl peptide chemotactic receptor reveal multiple important functional domains. J. Biol. Chem.* 268:25395; and Lavigne M C, Murphy P M, Leto T L, Gao J L. *The N-formylpeptide receptor (FPR) and a second G(i)-coupled receptor mediate fMet-Leu-Phe-stimulated activation of NADPH oxidase in murine neutrophils. Cell Immunol.* 2002 July-August; 218(1-2):7-12, each of which is incorporated by reference in its entirety.

Known ligand for FPR include several novel host-derived FPR ligands which are not formylated and do not show homology in their amino acid sequences. See, for example, Walther A, Riehemann K, Gerke V. *A novel ligand of the formyl peptide receptor: annexin I regulates neutrophil extravasation by interacting with the FPR. Mol. Cell.* 2000; 5:831-40; Le Y, Murphy P M and Wang J M (2002) Formylpeptide receptors revisited. *Trends Immunol.* 23:541-48; Murphy P M (1996) The N-formylpeptide chemotactic receptors, in "Chemoattractant ligands and their receptors" (Horuk R ed) pp 269, CRC Press, Inc., Boca Raton; and Prossnitz E R and Ye R D (1997) The N-formyl peptide receptor: a model for the study of chemoattractant receptor structure and function. *Pharmacol. Ther.* 74:73-102; each of which is incorporated by reference in its entirety. The only FPR agonist yet identified, Annexin I and its N-terminal peptides (AA1-26 and AA9-25), were verified using the FMLP antagonists (Boc-Met-Leu-Phe; Boc1, and Boc-Phe-Leu-Phe-Leu-Phe; Boc2, SEQ ID NO:8) on the anti-migratory activity of the annexin I peptides Ac1-26 and Ac9-25 (see Walther, A. et al. (2000) Mol. Cell. 5, 831-840).

Known ligands for FPR, FPRL1, and FPRL2 are listed in Table 1 (see, for example, Partida-Sanchez, S. *Chemotaxis and calcium responses of phagocytes to formyl peptide receptor ligands is differentially regulated by cyclic ADP ribose, J. Immunol.* 2004 Feb. 1; 172(3): 1896-906, which is incorporated by reference in its entirety).

TABLE 1

Host derived agonists

| Agonist | Derived from | target |
|---|---|---|
| MHC binding peptide | NADH dehydrogenase subunit I | FPRL1 |
| LL-37 | hCAP18 (aa1-37) | FPRL1 |
| Ac1-26 | annexin1 (aa1-26) | FPR |
| Ac9-25 | annexin1 (aa9-25) | FPR |
| D2D3$_{88-274}$ | uPAR (aa88-274) | FPRL1 |
| LXA4 | lipid metabolite | FPRL1, mLXA4R |
| SAA | acute phase protein | FPRL1, mFPR2 |
| Aβ$_{42}$ | APP (aa1-42) | FPRL1, mFPR2 |
| PrP106-126 | Prion (aa106-126) | FPRL1 |

A peptide fragment of NADH dehydrogenase subunit 1 having the sequence MYFINILTL (SEQ ID NO:2), is specific for FPRL1. See, for example, Chiang N, Fierro I M, Gronert K, Serhan C N. Activation of lipoxin A4 receptors by aspirin-triggered lipoxins and select peptides evokes ligand-specific responses in inflammation. *J. Exp. Med.* 2000; 191:1197-20, which is incorporated by reference in its entirety. LL-37 is chemotactic for, and can induce calcium mobilization in, human monocytes and formyl peptide receptor-like 1 (FPRL1)-transfected human embryonic kidney 293 cells. (see De Yang, LL-37, the Neutrophil Granule- and Epithelial cell-derived Cathelicidin, Utilizes Formyl Peptide Receptor-like 1 (FPRL1) as a Receptor to Chemoattract Human Peripheral Blood Neutrophils, Monocytes, and T Cells. *J. Exp. Med.* 192, 7, 1069-1074, which is incorporated by reference in its entirety).

FPRL1 binds serum amyloid A (SAA), Beta amyloid peptide, prion protein peptide, and the lipid metabolite lipoxin A. See, for example, Su, S B, et al., *Activation of a Chemoattractant Receptor FPRL1 by SAA, J. Exp. Med.* 189, 2, 395-402; and Partida-Sanchez, S., *J. Immunol.* 2004 Feb. 1; 172(3):1896-906, each of which is incorporated by reference in its entirety. A novel role for FPRL1 as a high-affinity b-chemokine receptor for an N-terminally truncated form of the CKb8 (also known as CCL23/MPIF-1) splice variant CKb8-1 (22-137 aa) has been described (see, for example, Elagoz A, et al., *A truncated form of CKbeta8-1 is a potent agonist for human formyl peptide-receptor-like 1 receptor.* Br J Pharmacol. 2004 January; 141(1):37-46, which is incorporated by reference in its entirety).

FPRL2 is expressed in monocytes but not in neutrophils, and is not activated by N-formylpeptides (see, e.g., Elagoz A, et al., *Br J Pharmacol.* 2004 January; 141(1):37-46, which is incorporated by reference in its entirety). Thus far, no ligands have been identified for FPRL2.

Further evidence a putative ligand interacts with the FPR receptor might be provided from the observation that the receptors, FPR and FPRL1, can be distinguished by their reliance on cyclic ADP ribose (cADPR) for calcium signaling (Partida-Sanchez, S., *J. Immunol.* 2004 Feb. 1; 172(3): 1896-906); this knowledge should provide an experimental method to demonstrate FPR specificity of the putative ligand.

The first extracellular loop and its adjacent transmembrane domains of FPR are essential for high affinity binding of fMLP. Information on the sequence and binding site structure of FPR is available. See, for example, Miettinen, H. M., et al. *The ligand binding site of the formyl peptide receptor maps in the transmembrane region. J. Immunol.* 1997 159:4045-4054; and Lala, A., et al., *Human formyl peptide receptor function role of conserved and nonconserved charged residues* Eur. J. Biochem. 254, 495-499, each of which is incorporated by reference in its entirety.

The human FPR exists in several isoforms (FPR-26, FPR-98 and FPR-G6). It has a molecular weight of 68 kDa. The FMLP receptor on human neutrophils has been reported to consist of multiple components, the major species being a glycoprotein of 55,000-70,000 Da. See, for example, Seifert R, and Wenzel-Seifert K, *The human formyl peptide receptor as model system for constitutively active G-protein-coupled receptors. Life Sci.* 2003 Sep. 19; 73(18):2263-80; Goetzl E J, (1981) *Biochemistry,* 20, 5717; Quehenberger O, Prossnitz ER, Cochrane C G and Ye R D, *Absence of G proteins in the Sf9 insect cell. Characterization of the uncoupled recombinant N-formyl peptide receptor.* J. Biol. Chem. 267: 19757-19760, 1992; and De Nardin E, Radel S J and Genco R J, *Isolation and partial characterization of the formyl peptide receptor components on human neutrophils. Biochem. Biophys. Res. Commun.* 174: 84-89, 1991, each of which is incorporated by reference in its entirety.

Deglycosylation with endoglycosidase F leaves a core peptide of ~33,000 Da, which is still able to bind the ligand. Isolation of a cDNA that codes for the human N-formylpeptide receptor has been reported. Using peptide analogs to different domains of the receptor, Radel et al. have shown that charged residues in the first extracellular loop play a critical role in ligand binding. See, for example, Lala, A., et al., *Recombinant expression and partial characterization of the human formyl peptide receptor. Biochim. Biophys. Acta* 1993, 1178, 302-306; Malech H L, et al., *Asparagine-linked oligosaccharides on formyl peptide chemotactic receptors of human phagocytic cells. J. Biol. Chem.* 260: 2509-2514, 1985; Boulay F, et al., *Synthesis and use of a novel N-formyl peptide derivative to isolate a human N-formyl peptide receptor cDNA. Biochem Biophys. Res. Commun.* 168: 1103-1109, 1990; Radel S J, et al. *Localization of Ligand-binding regions of human formyl peptide receptor. Biochem. Int.* 25: 745-753, 1991; and Radel S J, et al., *Structural and functional characterization of the human formyl peptide receptor ligand-binding region. Infect. Immunol.* 62: 1726-1732, 1994, each of which is incorporated by reference in its entirety.

Recombinant FPR was prepared by expression in *E. coli* followed by purification using gel filtration and affinity chromatography using an fMLP-Sepharose column and elution with FMLP resulting in approximately 1 mg yield and the recombinant FPR retained ligand binding capacity. Initial studies on the FPR ligand binding domains suggested that the ligand might occupy a hydrophobic pocket in the receptor. A synthetic 17-aa peptide (RKAMGGHWPFGWFLCKFl; SEQ ID NO:3), corresponding to residues 84 to 100 in the first extracellular domain of the FMLP receptor, was the strongest inhibitor of ligand binding to the 68-kDa protein. See, for example, Lala A, Sojar H T, De Nardin E, *Expression and Purification of Recombinant Human N-Formyl-L-leucyl+phenylalanine (FMLP) Receptor,* Biochemical Pharmacology, Vol. 54, pp. 381-390, 1997; Lala, A. & DeNardin, E. (1996) Role of Asp in ligand binding of human FMLP receptor. J. Dent. Res. 75, (Abstract 3204); Freer, R. J., et al. (1982) Formyl peptide chemoattractants: a model of the receptor on rabbit neutrophils. Biochemistry 21, 257-263; and Lala, A., et al., Biochim. Biophys. Acta 1993, 1178, 302-306, each of which is incorporated by reference in its entirety.

Functional studies of formyl peptide receptors have been performed by using neutrophils and monocytes, the expression of these receptors have been demonstrated in other cell types. For instance, hepatocytes, immature dendritic cells, astrocytes, microglial cells, and the tunica media of coronary arteries express the high-affinity FPR. While the chemoattractant activity has been demonstrated using a neutrophil model, it is important to recognize that FPR receptors are present elsewhere. Importantly, related to ACS, endogenous formyl peptides are released by eukaryotic mitochondria from necrotic cells and induce chemotaxis using FPR expressed by thrombin-activated platelets. See, e.g., McCoy R, et al. *N-formylpeptide and complement C5a receptors are expressed in liver cells and mediate hepatic acute phase gene regulation. J. Exp. Med.* 1995; 182:207-17; Sozzani S, et al. *Migration of dendritic cells in response to formyl peptides. C5a, and a distinct set of chemokines. J. Immunol.* 1995; 155:3292-5; Lacy M, et al. *Expression of the receptors for the C5a anaphylatoxin, interleukin-8 and FMLP by human astrocytes and microglia. J. Neuroimmunol.* 1995; 61:71-8; Keitoku M, et al. *FMLP actions and its binding sites in isolated human coronary arteries. J. Mol. Cell. Cardiol.* 1997; 29:881-94; and Czapiga M et al., *Human platelets exhibit chemotaxis using functional N-formyl peptide receptors. Exp. Hematol.* 2005 January; 33(1):73-84, each of which is incorporated by reference in its entirety.

N-formylmethionine peptides can be derived from invading bacteria, suggesting that a formylmethionine peptide present in the low mwt sample might be of bacterial origin (i.e., a contaminant). However, mitochondria are known to initiate protein synthesis with an N-formylmethionine residue, and preparations of disrupted human mitochondria or mitochondrial proteins cause neutrophil accumulation (see, for example, Carp H. *Mitochondrial N-formylmethionyl proteins as chemoattractants for neutrophils. J. Exp. Med.* 1982 Jan. 1; 155(1):264-75, which is incorporated by reference in its entirety). Mitochondria are usually considered to be the powerhouse of the cell and to be responsible for the aerobic production of ATP. However, many eukaryotic organisms are known to possess anaerobically functioning mitochondria, which differ significantly from classical aerobically functioning mitochondria. Mitochondrial ribosomal RNA sequences bear much more in common with bacteria than with ribosomes in the eukaryotic cytoplasm. For example, N-formylmethionyl transfer RNA has been found to exist only in mitochondria and bacteria. See, e.g., Yingying Le, Philip M. Murphy and J i Ming Wang, *Formyl-peptide receptors revisited; Trends in Immunology,* 23, 11, 541-548; and Dyer, Betsey Dexter and Robert Obar (editors), 1985. *The Origin of*

*Eukaryotic Cells*, Van Nostrand Reinhold Company, Inc., NY, each of which is incorporated by reference in its entirety.

In cardiac cells, mitochondria exist in two functionally distinct populations. Subsarcolemmal mitochondria are located beneath the plasma membrane, whereas interfibrillar mitochondria are present between the myofibrils; intracellular arrangement and regulation of mitochondrial respiration are tissue specific—in cardiac muscle, mitochondria are localized in the intermyofibrillar space at the level of the A-band of sarcomeres. See, for example, Palmer, J W, Tandler B, and Hoppel C L. *Biochemical properties of subsarcolemmal and interfibrillar mitochondria isolated from rat cardiac muscle. J. Biol. Chem.* 252: 8731-8739, 1977; and Boudina, S. et al., *Alteration of mitochondrial function in a model of chronic ischemia in vivo in rat heart. Am. J. Physiol. Heart Circ. Physiol.* 2002 March; 282(3):H821-31, each of which is incorporated by reference in its entirety.

In cardiac cells, mitochondria are located in functional complexes with sarcomeres and sarcoplasmic reticulum to achieve the most effective regulation of cellular energetics. These complexes, or intracellular energetic units (ICEUs) represent the basic pattern of organization of energy metabolism in cardiac and oxidative muscle cells. Mitochondria are arranged in a highly ordered crystal-like pattern in a muscle-specific manner. Structural connections between mitochondria and sarcomeres inside ICEUs are so strong that there exists a direct link between sarcomere length and regulation of mitochondrial function. Organization of mitochondria into ICEUs results in the heterogeneity of the intracellular diffusion of ADP (and ATP), a phenomenon which is in agreement with the general theories of the compartmentation of adenine nucleotides in the cardiac cells (see, for example, Vendelin, M., et al., *Mitochondrial regular arrangement in muscle cells: a "crystal-like" pattern, Am. J. Physiol. Cell Physiol.* 2005 March; 288(3):C757-67; and Saks, V. A., et al., *Intracellular energetic units in red muscle cells, Biochem. J.* 2001, 356, 643-657, each of which is incorporated by reference in its entirety).

In the normal cardiomyocyte, efficient energy transfer between cytosol and mitochondria depends on two organizational aspects of the mitochondrial isoenzyme of creatine kinase, which catalyses the forward reaction: Creatine+ATP→phosphocreatine+ADP. FIG. 1 schematically illustrates metabolic compartmentalization in cardiac cells. Functional coupling and compartmentation both depend strongly on the structure-function of the intermembrane space. Mitochondria in ischemic zones are dramatically changed with detachment of mitochondria from myofibrils leading to destruction of function. These alterations result in the impairment of intracellular energy transfer (channeling) from mitochondria to ATP-utilizing sites (see, e.g., Boudina, S. et al., *Am. J. Physiol. Heart Circ. Physiol.* 2002 March; 282(3): H821-31).

Energy production in the heart is mainly supported by mitochondrial function. Investigations have focused on mitochondrial alterations and energy production during acute ischemia and reperfusion in vitro. For example, ischemia followed by reperfusion is known to negatively affect mitochondrial function, by inducing a deleterious condition called mitochondrial permeability transition (MPT). The MPT is responsible for mitochondrial dysfunction and can ultimately lead to cell death. N-formylmethionine containing peptides are released from degenerating mitochondria at sites of tissue damage and this might play a role in the accumulation of inflammatory cells observed at these sites. It is plausible that the N-formylmethionine peptide Nourin-1 is derived from mitochondrial degradation. See, for example, Kay L, et al., *Alteration in the control of mitochondrial respiration by outer mitochondrial membrane and creatine during heart preservation. Cardiovasc Res.* 34: 547-556, 1997; Kay L, Rossi A, and Saks V. *Detection of early ischemic damage by analysis of mitochondrial function in skinned fibers. Mol. Cell. Biochem.* 174: 79-85, 1997; Kay L, Saks V A, and Rossi A. *Early alteration of the control of mitochondrial function in myocardial ischemia. J. Mol. Cell. Cardiol.* 29: 3399-3411, 1997; and Carp H., *J. Exp. Med.* 1982 Jan. 1; 155(1):264-75, each of which is incorporated by reference in its entirety.

Mitochondria are unique among organelles of animal cells in that they contain their own DNA (mitochondrial DNA, or mtDNA). Of the 37 genes that coded by mtDNA, 13 are translated into proteins, all of which are localized to the inner-mitochondrial membrane as components of the respiratory chain complexes (i.e., complexes I, II, III, IV and V; see, for example, *The human mitochondrial proteome: oxidative stress, protein modifications and oxidative phosphorylation Int. J. Biochem. Cell. Biol.* 2005 May; 37(5):927-34., which is incorporated by reference in its entirety). The respiratory chain includes complex I (NADH:ubiquinone oxidoreductase), complex II (succinate: ubiquinone oxidoreductase), complex III (ubiquinol:cytochrome c oxidoreductase), and complex IV (cytochrome c oxidase), which function together to generate an electrochemical potential across the inner mitochondrial membrane. Complex V ($F_1F_0$-ATP synthase) uses this electrochemical proton gradient to synthesize ATP. These complexes have been extensively studied, successfully purified and characterized, both at the proteomic and genomic level. See, for example, *The mitochondrial electron transport and oxidative phosphorylation system Annu. Rev. Biochem.* 1985; 54:1015-69; and *Assembly of respiratory complexes I, III, and IV into NADH oxidase supercomplex stabilizes complex I in Paracoccus denitrificans. J. Biol. Chem.* 2004 Feb. 6; 279(6):5000-7, each of which is incorporated by reference in its entirety.

Because mitochondria are present in animal cells, mitochondrial components (e.g., a mitochondrial polypeptide) can be detected in a sample taken from a subject animal, such as, for example, a human subject, or a non-human subject such as, for example, a bird, a mouse, a rat, a rabbit, a pig, a sheep, a goat, a cow, or another mammal.

The mitochondrial respiratory chain is a major source of reactive oxygen species (ROS) under pathological conditions including myocardial ischemia and reperfusion. Limitation of electron transport by the inhibitor rotenone immediately before ischemia decreases the production of ROS in cardiac myocytes and reduces damage to mitochondria. ROS are produced from mitochondrial complex I by the NADH dehydrogenase located in the matrix side of the inner membrane and are dissipated in mitochondria by matrix antioxidant defenses. See, for example, Chen Q, et al. *Production of reactive oxygen species by mitochondria: central role of complex III. J. Biol. Chem.* 2003 Sep. 19; 278(38):36027-31, which is incorporated by reference in its entirety. ROS contribute to a number of pathological processes including aging, apoptosis, and cellular injury during ischemia and reperfusion. The mitochondrial electron-transport chain is the main source of ROS during normal metabolism. The rate of ROS production from mitochondria is increased in a variety of pathologic conditions including hypoxia, ischemia, and reperfusion. Most of the ROS radicals are produced at Complex I, and high rates of production of ROS are features of respiratory chain-inhibited mitochondria and of reversed electron flow arising in conditions of ischemia (see, e.g., Kudin A P, et al. *Characterization of superoxide-producing sites in isolated brain mitochondria. J. Biol. Chem.* 2004 Feb. 6; 279(6):4127-35, which is incorporated by reference in its entirety).

Complex I is the entry point for electrons into the respiratory chains of many bacteria and mitochondria of most eukaryotes. It couples electron transfer with the translocation of protons across the membrane, thus providing the proton motive force essential for energy-consuming processes. Following two-dimensional SDS-PAGE and electroblotting, a mixture of specific antibodies was used to identify the location of assembled complexes and dissociated subunits purified from mitochondria. Antibodies identified supercomplexes a, b, and c and individual complexes III and IV, but intact individual Complex I was not present. Complex I is stabilized by super-assembly into the NADH oxidase complex and appears to easily dissociate. See, for example, *J. Biol. Chem.* 2004 Feb. 6; 279(6):5000-7, which is incorporated by reference in its entirety.

Figure 2:
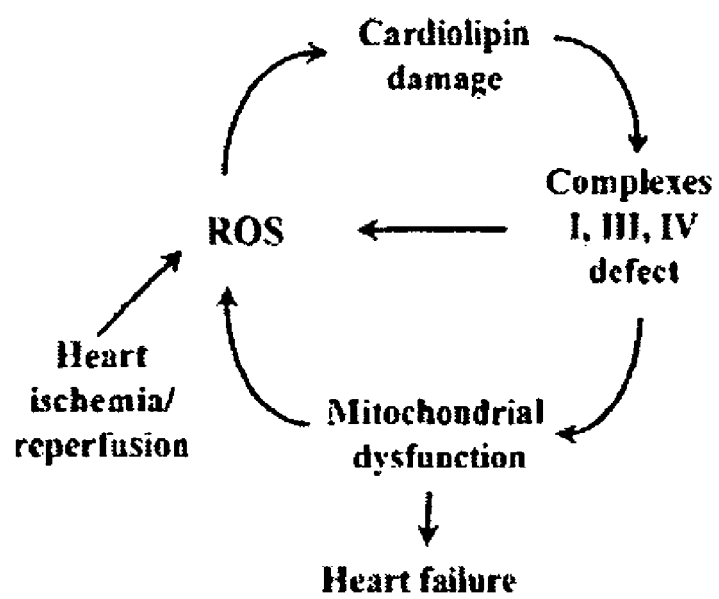
FIG. 2 is a schematic diagram depicting the link between reactive oxygen species, mitochondrial complex defects, and mitochondrial dysfunction.

The activity of complex I is reduced in mitochondria isolated from ischemic and reperfused rat heart. The mitochondrial content of cardiolipin, which is required for optimal activity of complex I, decreases as function of ischemia and reperfusion. Cardiolipin is recognized as a relatively early target of ischemic mitochondrial damage. The simple model illustrated in FIG. 2 summarizes the link between ROS, mitochondrial complex defects, and mitochondrial dysfunction. See, for example, Paradies G, et al., *Decrease in mitochondrial complex I activity in ischemic/reperfused rat heart: involvement of reactive oxygen species and cardiolipin. Circ. Res.* 2004 Jan. 9; 94(1):53-9, which is incorporated by reference in its entirety.

Figure 3:
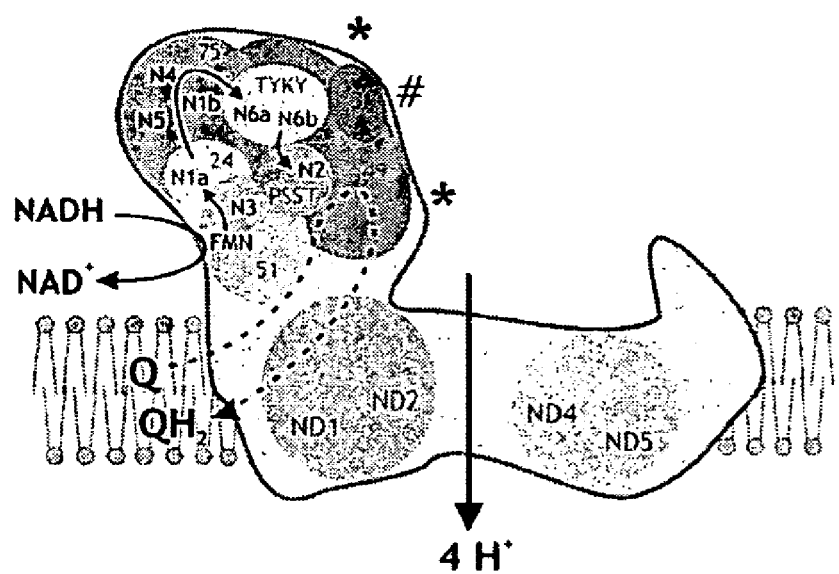
FIG. 3 is a schematic diagram of the arrangement of subunits in mitochondrial complex I.

Mitochondrial complex I catalyzes electron transfer from NADH to ubiquinone in a process coupled to proton transport across the inner mitochondrial membrane. Complex I is made of more than 30 subunits, the majority of which are encoded by nuclear genes and imported from the cytoplasm. However, seven subunits are coded for by mitochondrial genes (ND1, -2, -3, -4, -4L, -5, and -6; see, e.g., Remacle C, et al. *Mutants of Chlamydomonas reinhardtii deficient in mitochondrial complex I: characterization of two mutations affecting the nd1 coding sequence. Genetics* 2001 July; 158(3):1051-60, which is incorporated by reference in its entirety). An arrangement of the subunits is shown in FIG. 3; Table 2 summarizes the nomenclature for the subunits found in mammals, bacteria, and yeast.

TABLE 2

| Complex I subunit symbol | | |
|---|---|---|
| Bovine | *Y. lipolytica* | *E. coli* |
| 75 kDa | NUAM | NuoG |
| 51 kDa | NUBM | NuoF |
| 49 kDa | NUCM | NuoD |
| 30 kDa | NUGM | NuoC |
| 24 kDa | NUHM | NuoE |
| TYKY | NUIM | NuoI |
| PSST | NUKM | NuoB |
| ND1 | ND1 | NuoH |
| ND2 | ND2 | NuoN |
| ND3 | ND3 | NuoA |
| ND4 | ND4 | NuoM |
| ND4L | ND4L | NuoK |
| ND5 | ND5 | NuoL |
| ND6 | ND6 | NuoJ |

Release of mitochondrial proteins has been proposed as a sensitive indicator of cellular damage that might result in mitochondrial proteins into the circulation. Importantly, proteomic analysis of ischemic hearts revealed profound changes in enzymes related to energy metabolism, e.g., NADH dehydrogenase and ATP synthase, with partial fragmentation of these mitochondrial enzymes. An amino acid sequence of the NADH dehydrogenase subunit 1 (ND1) was found to exhibit FPR-binding properties. See, for example, Shawar S M, et al. *Peptides from the amino-terminus of mouse mitochondrially encoded NADH dehydrogenase subunit* 1 are potent chemoattractants. Biochem. Biophys. Res. Commun. 1995 Jun. 26; 211 (3):812-8; and Mayr M, et al. *Ischemic preconditioning exaggerates cardiac damage in PKC-delta null mice. Am. J. Physiol. Heart Circ. Physiol.* 2004 August; 287(2):H946-56, each of which is incorporated by reference in its entirety.

The N-terminus of ND1 was found to have significant chemotactic activity (see, e.g., Shawar S M, et al. *Biochem. Biophys. Res. Commun.* 1995 Jun. 26; 211(3):812-8). The ND1 peptide is believed to interact with FPRL1 and not FPR (see, e.g., Chiang N, et al. *J. Exp. Med.* 2000; 191: 1197-207).

The N-terminus of Peptide 3 (MIINHNLAAINSHR; (SEQ ID NO:4); see U.S. patent application Ser. No. 10/945,442, which is incorporated by reference in its entirety) is similar to that of ND1: specifically, it features an N-terminal methionine followed by two hydrophobic amino acids. Note that Freer suggested that the ligand for FPR occupies a hydrophobic pocket in the receptor (Freer, R. J., et al. (1982) Formyl peptide chemoattractants: a model of the receptor on rabbit neutrophils. Biochemistry 21, 257-263, which is incorporated by reference in its entirety).

| Peptide | Sequence |
|---|---|
| fMLP | fMLF |
| ND1α$_{1-12}$ | MFFINILTLLVP (SEQ ID NO:5) |
| Peptide 3 | MIINHNLAAINSHR (SEQ ID NO:4) |

Through reductive evolution, the complement of genes constituting the original eubacterial predecessors of modern-day mitochondria have been either lost or transferred from mtDNA to the nuclear genome (see, for example, Andersson, S. G (1998). *The genome sequence of Rickettsia prowazekii and the origin of mitochondria. Nature* 396, 133-140, which is incorporated by reference in its entirety). The mitochondrion has also acquired new proteins and functionality. A systematic survey of mitochondrial proteins from brain, heart, kidney, and liver of C57BL6/J mice was performed by Mootha. Mitochondrial proteins from each tissue were solubilized and size separated by gel filtration into a batch of approximately 15-20 fractions. These proteins were then digested and analyzed by liquid chromatography; the proteins varied in molecular weight and isoelectric point. An important finding was a high percentage of hydrophobic and membrane proteins that had up to now been seriously underrepresented by 2-DE gel protocols. See, for example, *Integrated Analysis of Protein Composition, Tissue Diversity, and Gene Regulation in Mouse Mitochondria Cell*, Vol. 115, 629-640, Nov. 26, 2003; and *The human mitochondrial proteome: oxidative stress, protein modifications and oxidative phosphorylation The International Journal of Biochemistry & Cell Biology* 37 (2005) 927-93, each which is incorporated by reference in its entirety.

A mitochondrial protein sequence database (MitoProteome) was generated from experimental evidence and public databases, and containing both mitochondrial- and nuclear-encoded entries. The initial release contains 847 human mitochondrial proteins, 615 of which were experimentally determined by mass spectrometry. See, e.g., Steven W. Taylor, et al. *Characterization of the human heart mitochondrial proteome. Nature Biotechnology* 2003, 21, 3 pp 281-286, which is incorporated by reference in its entirety. Less than 5% of the encoded proteins have a mwt of less than 10 kDa.

For example, two of the low mwt mitochondrial proteins identified from human mitochondria are:

NADH dehydrogenase (ubiquinone) 1 beta subcomplex, 1, 7 kDa; NADH dehydrogenase (ubiquinone) 1 beta subcomplex, 1 (7 kD, MNLL) (*Homo sapiens*), sequence: MICWRHPSAPCGRGEWQVPRSQL-PLARVEFPVALGLGVAVGAEAAAIMVN LLQIVRDH-WVHVLVPMGFVIGCYLDRKSDER-LTAFRNKSMLFKRELQPSEEVTWK (SEQ ID NO:6)

Cytochrome c oxidase subunit VIIc precursor; cytochrome-c oxidase chain VIIc (*Homo sapiens*), sequence:

MLGQSIRRFTTSVVRRSHYEEGPGKN-
LPFSVENKWSLLAKMCLYFGSAFA TPFLV-
VRHQLLKT (SEQ ID NO:7).

Nourin-1 can be released from mitochondria as a consequence of mitochondrial disruption. Because mitochondrial disruption is a feature of cardiac damage, detection of elevated levels of Nourin-1 in a sample (for example, a blood sample), can be diagnostic for cardiac damage (e.g., acute coronary syndrome). See, for example, U.S. patent application Ser. No. 10/945,442, filed Sep. 21, 2004, which is incorporated by reference in its entirety. The neutrophil chemotactic effects of Nourin-1 can be a result of a nonspecific anti-bacterial response to N-formyl peptides.

The chemokines are 8-14 kDa-secreted cytokines, and four subfamilies have been discovered including: CXC(a), CC(b), C(g) and CX3C. Haddad has summarized currently known cytokines and their receptors (see Table 3 below, and Murphy P M, et al. (2000). *International union of pharmacology. XXII. Nomenclature for chemokine receptors. Pharmacol Rev.* 52: 145-176; and *Cytokines and related receptor-mediated signaling pathways Biochem. Biophys. Res. Commun.* 2002 Oct. 4; 297(4):700-13, each of which is incorporated by reference in its entirety). Most cytokines are unrelated in terms of sequence, although some can be grouped into families or are classified into categories according to the types of secondary and tertiary structure. IFN-α, IFN-β, IFN-X, IL-2, IL-3, IL-4, IL-5, IL-6, IL-7, IL-9, G-CSF, M-CSF, GM-CSF, and PDGF, for example, have α-helical secondary structure. Beta-structural cytokines include IL-1a, IL-1b, TNF-α, TNF-β, and FGF. Composite structures (α and β) are observed with IL-8, IFN-α, IP-10, PF-4, GRO, and 9E3. While none of these cytokines have molecular weights of <3 kDa, data published results on Lkn-1, CKb8 and other CC chemokines (i.e., HCC1, MCP-1, MCP-2, MIP-1b), suggest that the processing of the N-terminus of some members of b-chemokines, including CKb8-1, may represent a novel mechanism to increase the diversity of inflammatory effects inherent to these ligands. See, for example, Elagoz A, et al. *A truncated form of CKbeta8-1 is a potent agonist for human formyl peptide-receptor-like 1 receptor. Br. J. Pharmacol.* 2004 January; 141(1):37-46, which is incorporated by reference in its entirety. It is possible that Nourin-1 is a ligand released from a high mwt species.

TABLE 3

Structural families of cytokines and cytokine receptors

| Cytokine family | Members | Receptor type |
|---|---|---|
| Haematopoietins (four α-helical bundles) | IL-2, IL-3, IL-4, IL-5, IL-6, IL-7, IL-9, IL-13, G-CSF, GM-CSF, CNTF, OSM, LIF, and EPO | Cytokine receptor class I |
|  | IL-10, IFN-α, IFN-β, and IFN-γ | Cytokine receptor class II |
|  | M-CSF | Tyrosine kinase |
| EGF (β-sheet) | EGF and TGF-α | Tyrosine kinase |
| β-Trefoil | FGF-α and FGF-β | Split tyrosine kinase |
|  | IL-1α, IL-1β, and IL-1ra | IL-1 receptor |
| TNF (Jelly roll motif) | TNF-α, TNF-β, LT-β | NGF/TNF receptor |
| Cysteine knot | NGF | NGF/TNF receptor |
|  | TGF-$β_1$, TGF-$β_2$, TGF-$β_3$ | Serine/threonine kinase |
|  | PDGF and VEGF | Tyrosine kinase |
| Chemokines (triple-stranded. anti-parallel β-sheet in Greek key motif) | IL-8, MIP-1α, MIP-1β, MIP-2, PF-4, PBP, I-309/TCA-3, MCP-1, MCP-2, MCP-3, γIP-10 | Rhodopsin superfamily |

Other embodiments are within the scope of the following claims.

What is claimed is:

1. A method of detecting ischemia comprising:
obtaining a sample from a subject suspected to have ischemia; and
assaying the sample for Nourin-1 using one or more formyl peptide receptors (FPRs) or fragments thereof comprising the sequence RKAMGGHWPFGWFLCKF (SEQ ID NO:3) to bind the Nourin-1,
wherein an elevated level of the Nourin-1 compared to normal, healthy subjects is indicative of ischemia.

2. The method of claim 1, wherein the Nourin-1 is an N-formyl polypeptide.

3. The method of claim 1, wherein the Nourin-1 is a tissue-derived Nourin.

4. A method of detecting ischemia comprising:
obtaining a sample from a subject suspected to have ischemia; and
assaying the sample for an N-formyl Nourin-1 using a formyl peptide receptor (FPR) or fragments thereof comprising the sequence RKAMGGHWPFGWFLCKF (SEQ ID NO:3) to detect binding of the receptor or fragments thereof to the N-formyl Nourin-1,
wherein an elevated level of the N-formyl Nourin-1 as compared to normal, healthy subjects is indicative of ischemia.

5. The method of claim 4, wherein the N-formyl Nourin-1 is a mitochondrial polypeptide.

6. The method of claim 4, wherein the N-formyl Nourin-1 is a tissue-derived Nourin.

7. The method of claim 4, wherein the ischemia is reversible.

8. The method of claim 1, wherein the ischemia is reversible.

9. The method of claim 1, wherein the Nourin-1 is mitochondrial.

10. The method of claim 1, wherein the sample is assayed using a naturally occurring isoform of human FPR.

* * * * *

SEQUENCE LISTING

```
<160> NUMBER OF SEQ ID NOS: 8

<210> SEQ ID NO 1
<211> LENGTH: 7
<212> TYPE: PRT
<213> ORGANISM: Homo sapiens

<400> SEQUENCE: 1

Leu Val Val Tyr Pro Trp Thr
1               5

<210> SEQ ID NO 2
<211> LENGTH: 9
<212> TYPE: PRT
<213> ORGANISM: Homo sapiens

<400> SEQUENCE: 2

Met Tyr Phe Ile Asn Ile Leu Thr Leu
```

<210> SEQ ID NO 3
<211> LENGTH: 17
<212> TYPE: PRT
<213> ORGANISM: Artificial Sequence
<220> FEATURE:
<223> OTHER INFORMATION: FMLP receptor derived peptide

<400> SEQUENCE: 3

Arg Lys Ala Met Gly Gly His Trp Pro Phe Gly Trp Phe Leu Cys Lys
1               5                   10                  15

Phe

<210> SEQ ID NO 4
<211> LENGTH: 14
<212> TYPE: PRT
<213> ORGANISM: Artificial Sequence
<220> FEATURE:
<223> OTHER INFORMATION: N-terminus of Peptide 3

<400> SEQUENCE: 4

Met Ile Ile Asn His Asn Leu Ala Ala Ile Asn Ser His Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Sequence from NADH dehydrogenase subunit 1

<400> SEQUENCE: 5

Met Phe Phe Ile Asn Ile Leu Thr Leu Leu Val Pro
1               5                   10

<210> SEQ ID NO 6
<211> LENGTH: 105
<212> TYPE: PRT
<213> ORGANISM: Homo sapiens

<400> SEQUENCE: 6

Met Ile Cys Trp Arg His Pro Ser Ala Pro Cys Gly Arg Gly Glu Trp
1               5                   10                  15

Gln Val Pro Arg Ser Gln Leu Pro Leu Ala Arg Val Glu Phe Pro Val
            20                  25                  30

Ala Leu Gly Leu Gly Val Ala Val Gly Ala Glu Ala Ala Ala Ile Met
        35                  40                  45

Val Asn Leu Leu Gln Ile Val Arg Asp His Trp Val His Val Leu Val
    50                  55                  60

Pro Met Gly Phe Val Ile Gly Cys Tyr Leu Asp Arg Lys Ser Asp Glu
65                  70                  75                  80

Arg Leu Thr Ala Phe Arg Asn Lys Ser Met Leu Phe Lys Arg Glu Leu
                85                  90                  95

Gln Pro Ser Glu Glu Val Thr Trp Lys
            100                 105

<210> SEQ ID NO 7
<211> LENGTH: 63
<212> TYPE: PRT
<213> ORGANISM: Homo sapiens

<400> SEQUENCE: 7

-continued

```
Met Leu Gly Gln Ser Ile Arg Arg Phe Thr Thr Ser Val Val Arg Arg
1               5                   10                  15

Ser His Tyr Glu Glu Gly Pro Gly Lys Asn Leu Pro Phe Ser Val Glu
                20              25                  30

Asn Lys Trp Ser Leu Leu Ala Lys Met Cys Leu Tyr Phe Gly Ser Ala
            35              40                  45

Phe Ala Thr Pro Phe Leu Val Val Arg His Gln Leu Leu Lys Thr
        50              55                  60

<210> SEQ ID NO 8
<211> LENGTH: 5
<212> TYPE: PRT
<213> ORGANISM: Artificial Sequence
<220> FEATURE:
<223> OTHER INFORMATION: fMLP antagonist peptide

<400> SEQUENCE: 8

Phe Leu Phe Leu Phe
1               5
```